United States Patent [19]

Carol

[11] Patent Number: 5,207,688

[45] Date of Patent: May 4, 1993

[54] NONINVASIVE HEAD FIXATION METHOD AND APPARATUS

[75] Inventor: Mark P. Carol, Milford, N.Y.

[73] Assignee: Medco, Inc., Cinnaminson, N.J.

[21] Appl. No.: 785,827

[22] Filed: Oct. 31, 1991

[51] Int. Cl.$^5$ .................................. A61B 19/00
[52] U.S. Cl. ..................... 606/130; 606/1; 604/116
[58] Field of Search ............. 606/1, 130; 604/116

[56] References Cited

U.S. PATENT DOCUMENTS

| | | | |
|---|---|---|---|
| 4,463,758 | 8/1984 | Patil et al. | 606/130 |
| 4,550,713 | 11/1985 | Hyman | 606/130 |

FOREIGN PATENT DOCUMENTS

| | | | |
|---|---|---|---|
| 2724321 | 12/1977 | Fed. Rep. of Germany | 606/130 |
| 3627510 | 2/1988 | Fed. Rep. of Germany | 606/130 |
| 1342478 | 10/1987 | U.S.S.R. | 606/130 |
| 2213066 | 8/1989 | United Kingdom | 606/130 |

OTHER PUBLICATIONS

Calergo ® Moldable Immobilizer/Positioner ad.
MOLD-and-HOLD ® Immobilizer/Positioner ad.
Bite Block System/with Nasal and Bridge Positioners ad.
ORFIT ® Immobilization System ad.
The Laitinen Stereotactic System brochure.

*Primary Examiner*—Stephen C. Pellegrino
*Assistant Examiner*—Glenn Dawson
*Attorney, Agent, or Firm*—Ben D. Tobor

[57] ABSTRACT

A noninvasive head fixation method and apparatus uses a flexible and compressible bladder which contacts and is deformed to conform to the shape of the patient's nasion in order to immobilize the patient's head during a medical procedure.

32 Claims, 5 Drawing Sheets

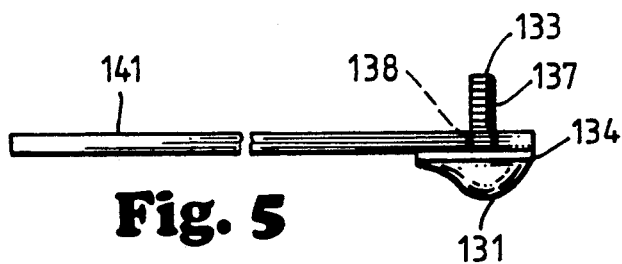
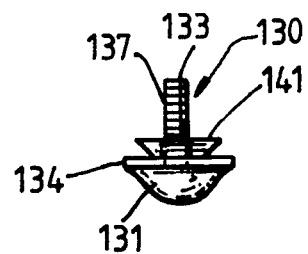
Fig. 5
Fig. 6
Fig. 7
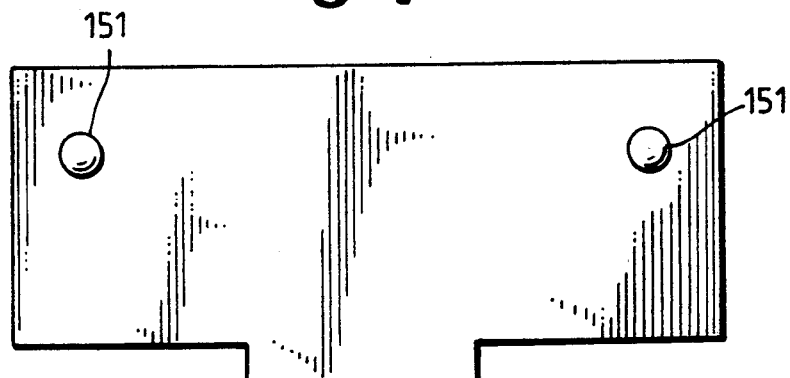
Fig. 6A
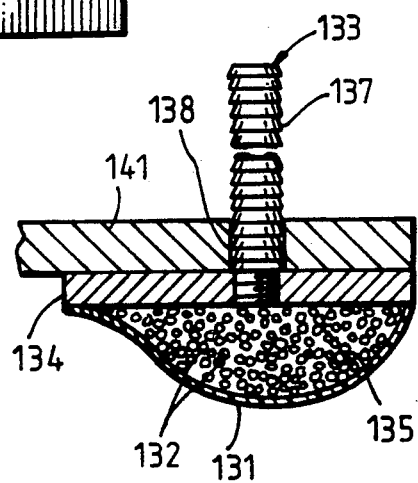
Fig. 8
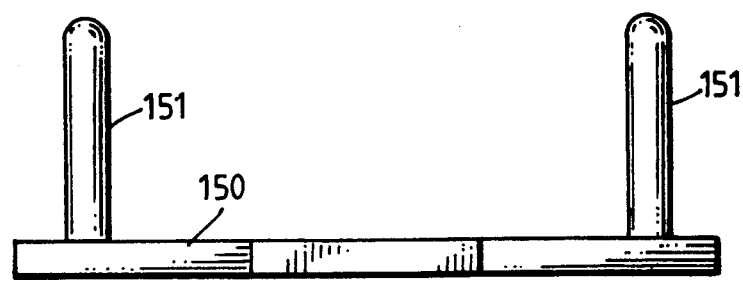

NONINVASIVE HEAD FIXATION METHOD AND APPARATUS

BACKGROUND OF THE INVENTION

1. Field of the Invention

The invention relates to a noninvasive head fixation method and apparatus for use in medical procedures to immobilize the head of a patient.

2. Description of the Prior Art

In many types of medical procedures, it is necessary to immobilize the patient's head during the medical procedure. When imaging a patient with almost any form of radiographic technique, immobilization of the patient's head is required. The imaging procedure requires a particular amount of time, and movement during that period of time may distort the image. It is also sometimes necessary to immobilize the patient's head so that the information obtained from the imaging procedure can be used at a later point in time, such as during a stereotactic procedure. In the case of a stereotactic procedure, the coordinates of a point inside the brain, which are obtained from the imaging procedure, are translated to a stereotactic apparatus attached and secured to the patient's head, so as to allow the surgeon to access a particular point either surgically or with radiation therapy. The head must not only be immobilized during the imaging procedure, but it also needs to be immobilized in the same orientation during the therapeutic procedure, such as stereotactic surgery or radiation therapy, that it had during the imaging procedure.

The patient's head must also be immobilized during cranial surgery. When precise stability and/or immobilization of the patient's head is not required during cranial surgery, noninvasive head fixation devices are often utilized to immobilize the head. If the particular surgical procedures requires delicate and precise manipulations by the surgeon, such as when a microscope is utilized, the patient's head is normally fixated through the use of an invasive head fixation device, which typically involves securing a frame to the patient's head with pins, and then clamping the frame to the imaging table or operating room table. Another form of invasive head fixation typically involves securing a plate to the patient's skull by a plurality of screws, and then securing the plate to a bracket disposed upon the imaging table or operating table.

Various types of noninvasive head fixation methods and apparatus are presently in use. Most commonly, the patient's head is secured to an imaging table with foam blocks and tape. In another system, a bite block or nasal bridge block is attached to a rod secured to an imaging table. The patient bites on the bite block while the imaging occurs, or the patient is held in place by the bridge block. In another system, the patient has an apparatus attached to his or her head for use with a nose bridge device and two ear plugs. In one system a plastic mold of the head is made, using a heat moldable material, and the plastic mold is disposed over the patient's head and is attached to the imaging table.

Of the many disadvantages associated with invasive head fixation systems, the following disadvantage is a major disadvantage. In the case of stereotactic radiosurgical procedures, a patient may require up to thirty or forty of these treatments over a six week period of time. It is not desirable to have such a patient carry a metal frame or plate upon their head during that six week period of time, in order to maintain the same orientation of the frame or plate upon the patient's head.

As to presently used noninvasive head fixation methods and apparatus, the use of a bite block can result in slightly different orientations of the patient's head with respect to the imaging or operating room table. Additionally, sanitary issues are presented by the repeated use of the bite block in repeated procedures. Additionally, bite blocks cannot be used in procedures wherein it is desired to intubate the patient, as well as such use presenting problems for patients who have difficult breathing through their nose. The use of nasal bridge blocks, because it is a generic design, makes it difficult to adequately conform the bridge block to a patient's anatomy and thus makes it extremely difficult to be precise in repositioning the patient to maintain the same orientation of the patient's head with respect to the imaging table or operating room table, during subsequent procedures.

There are additional disadvantages associated with plastic molds, in that the entire face of the patient is typically covered by the plastic material. Holes must be cut for the patient's eyes, ears, nose, and mouth, which is a time consuming process, as well as does not permit the patient to be intubated. Additionally, stereotactic invasive procedures of the patient's skull are also difficult and cumbersome to perform when this type of fixation is utilized. When the fixation system utilizing a nose bridge and two ear plugs is utilized, intubation of the patient is limited, and the associated framework prevents the use of many surgical approaches to the patient's skull.

Accordingly, prior to the development of the noninvasive head fixation method and apparatus, there has been no noninvasive head fixation method and apparatus which: is easy to use, and does not require an excessive amount of set-up time; permits the patient's head to maintain the same orientation with respect to an imaging or operating room table throughout a plurality of medical procedures; allows for intubation of the patient; and is readily usable in a wide range of surgical and nonsurgical techniques. Therefore, the art has sought a noninvasive head fixation method and apparatus which: is easy to use, and does not require an excessive amount of set-up time; permits the orientation of the patient's head with respect to an imaging or operating room table to be readily reproduced for a number of subsequent medical procedures to be done over a period of time; permits intubation of the patient; and is usable in a wide range of surgical and nonsurgical techniques.

SUMMARY OF THE INVENTION

In accordance with the invention, the foregoing advantages have been achieved through the present noninvasive head fixation device for use in medical procedures to immobilize the head of a patient having a nasion. The noninvasive head fixation device, in accordance with the present invention, includes: a frame, adapted to be disposed adjacent to the patient's head; a first deformable housing associated with the frame, the first deformable housing adapted to overlie and contact the patient's nasion and to deform and conform to the shape of the patient's nasion, the first deformable housing including means for retaining the shape imparted to the first deformable housing by the patient's nasion; and means for restraining rotational movement of the patient's head, the restraining means being associated with the frame.

Another feature of the present invention is that the first deformable housing may include a flexible and compressible bladder which can conform to the shape of the patient's nasion. A further feature of the present invention is that the bladder may be fluid tight and contain a plurality of small diameter beads which are movable within the bladder to permit the bladder to conform to the shape of the patient's nasion.

Another feature of the present invention is that the shape retaining means may include a valve in fluid communication with the bladder, whereby a vacuum may be created in the bladder to retain the imparted shape by prohibiting movement of the plurality of beads contained within the bladder. An additional feature of the present invention is that means for adjustably positioning the first deformable housing with respect to the frame and the patient's nasion may be provided. The adjustable positioning means may also include an elongate bar member slidable within the frame and include means for securing the bar member with respect to the frame.

Another feature in accordance with the present invention is that the restraining means may comprise at least one second deformable housing associated with the frame and adapted to contact a portion of the patient's head, and may include a flexible compressible bladder which can conform to the shape of the portion of the patient's head which contacts the deformable housing. A further feature of the present invention is that the at least one second deformable housing may be a compressible bladder mounted upon the frame and is disposed in a diametrically opposed relationship from the first deformable housing and is adapted to contact the underside of the patient's head. A further feature of the present invention is that the at least one second deformable housing may be two compressible bladders mounted upon the frame, each of the two compressible bladders being disposed in a plane which is disposed substantially perpendicular to a plane in which lies the first deformable housing, whereby the two compressible bladders of the second deformable housing contact the sides of the patient's head.

In accordance with the present invention, the foregoing advantages have also been achieved through the present noninvasive method of immobilizing a head of a patient having a nasion, for use in medical procedures. The method, in accordance with the present invention, includes the steps of: disposing the patient's head adjacent a frame; disposing a first deformable housing associated with the frame to overlie and contact the patient's nasion; deforming the first deformable housing to conform to the patient's nasion; retaining the shape imparted to the first deformable housing by the patient's nasion; and restraining rotational movement of the patient's head.

A further feature of the present invention includes the step of utilizing a flexible and compressible bladder as the first deformable housing. Another feature of the present invention may include the step of making the bladder fluid tight and filling the bladder with a plurality of small diameter beads which are movable within the bladder. An additional feature of the present invention includes the steps of disposing a valve in fluid communication with the bladder; and creating a vacuum in the bladder to retain the imparted shape by prohibiting movement of the plurality of beads contained within the bladder.

An additional feature of the present invention includes the steps of removing the patient's head from adjacent the frame, after completing the medical procedure; later disposing the patient's head adjacent the frame for a second medical procedure; disposing a first deformable housing associated with the frame to overlie and contact the patient's nasion, the first deformable housing having a shape previously imparted to it by the patient's nasion; and restraining rotational movement of the patient's head. An additional feature of the present invention may include the step of forming an impression of the first deformable housing having retained the shape imparted to it by the patient's nasion during a first medical procedure, whereby the impression can be later used as a mold to permit another deformable housing to be formed, for use in a second medical procedure, in the shape of the patient's nasion during the first medical procedure.

The noninvasive head fixation method and apparatus of the present invention, when compared with previously proposed prior art methods and apparatus, have the advantages of being: easy to use, without requiring an excessive amount of set-up time; permits the patient's head to be disposed in the same orientation with respect to an imaging or operating room table, in subsequent procedures, as it had during the first medical procedure; allows for intubation of the patient; and is usable in a wide range of surgical and nonsurgical techniques.

BRIEF DESCRIPTION OF THE DRAWINGS

In the drawings:

FIG. 5 is a side view of a deformable housing mounted on an elongate bar member in accordance with the present invention;

FIG. 6 is a front view of the deformable housing and elongate bar member of FIG. 5;

FIG. 6A is a partial, exploded view of a deformable housing, in accordance with the present invention;

FIG. 7 is a top view of a base member used with the device of FIG. 1, in accordance with the present invention;

FIG. 8 is a front view of the base member of FIG. 7, in accordance with the present invention;

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined in the appended claims.

DETAILED DESCRIPTION OF THE INVENTION

Figure 1:
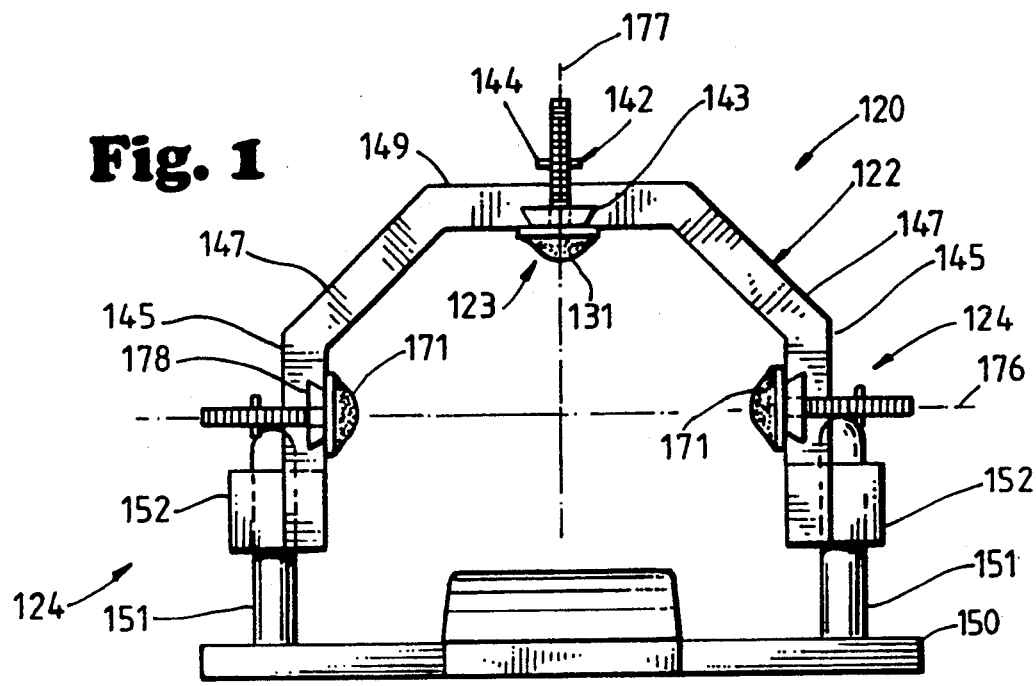
FIG. 1 is a front view of the noninvasive head fixation device of the present invention.
Figure 2:
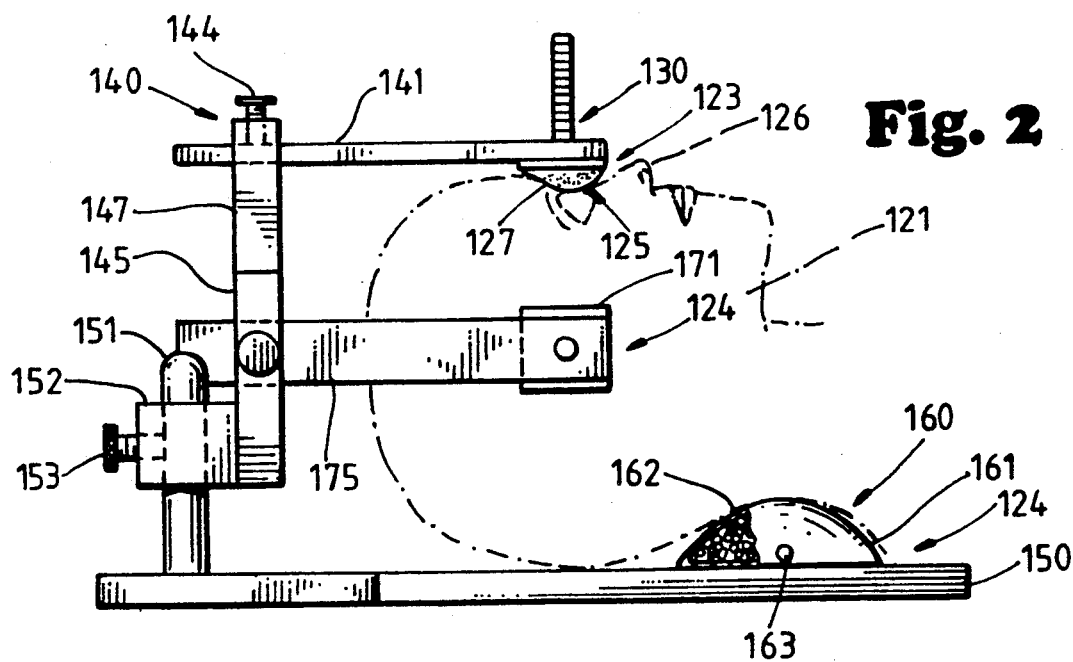
FIG. 2 is a side view of the device of FIG. 1, a patient's head being shown in phantom lines.
Figure 3:
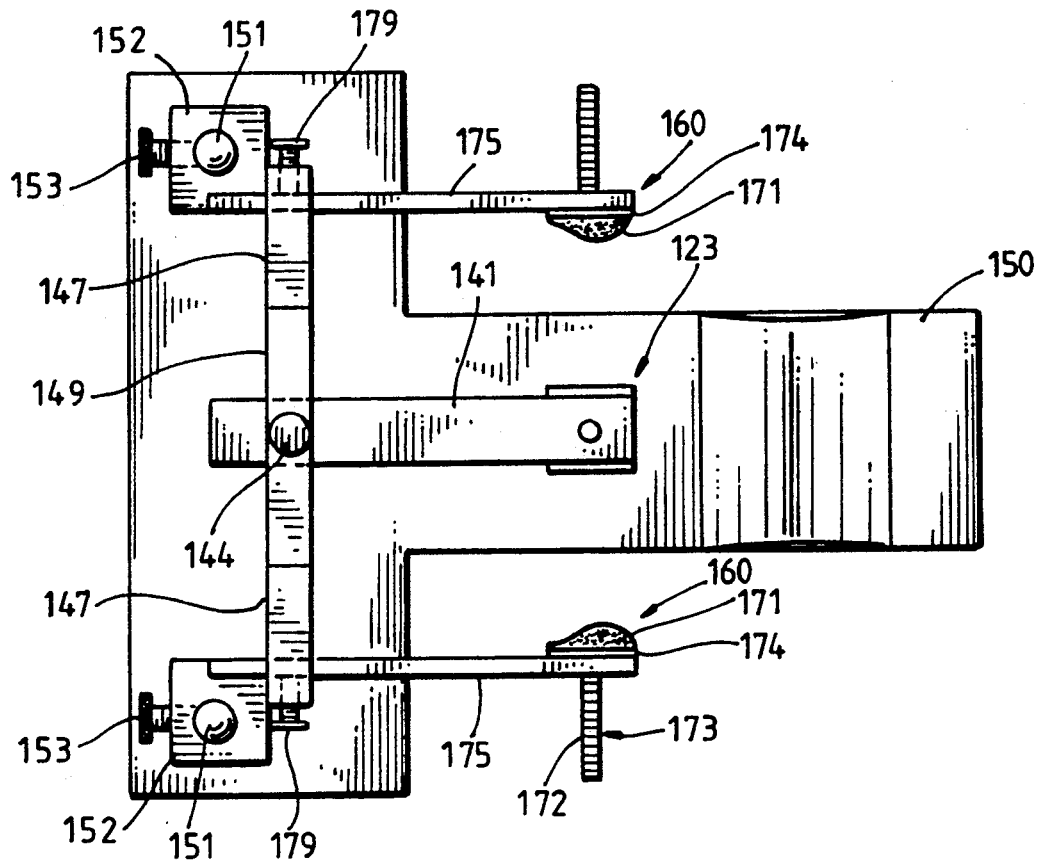
FIG. 3 is a top view of the device of FIG. 1.

With reference to FIGS. 1-3, the noninvasive head fixation device 120 for use in medical procedures to immobilize a patient's head 121, in accordance with the present invention, generally comprises: a frame 122, adopted to be disposed adjacent the patient's head 121; a first deformable housing 123 associated with the frame 122; and means for restraining 124 rotational movement of the patient's head 121, the restraining means 124 being associated with the frame 122. The patient's head 121 has a nasion 125, or the bridge of the patient's nose 126 where it joins the patient's forehead 127 The first deformable housing 123 is adapted to overlie and contact the patient's nasion 125 and to form and conform to the shape of the patient's nasion 125 as will be hereinafter described in greater detail. The first deformable housing 123 further includes means for retaining 130 the shape imparted to the first deformable housing 123 by the patient s nasion 125, as will also be hereinafter described in greater detail. The first deformable housing 123 preferably includes a flexible and compressible bladder 131 (FIGS. 6 and 6A) which can conform to the shape of the patient's nasion, the bladder 131 being preferably fluid tight and containing a plurality of small diameter beads 132 which are movable within the bladder 131 to permit the bladder 131 to conform to the shape of the patient's nasion, upon the bladder 131 being pressed against the nasion 125.

As seen in FIGS. 6 and 6A, shape retaining means 130 includes a valve 133 in fluid communication with the interior 135 of bladder 131. As previously described, bladder 131 is fluid tight and includes a bottom plate member 134 upon which bladder 131 is fixedly secured as by heat welding, epoxy glue, or any other suitable means to fixedly secure flexible bladder 131 to bottom plate member 134. Prior to bladder 131 being secured to bottom plate member 134, the plurality of small diameter beads 132 are placed within the interior 135 of bladder 131. Preferably, bladder 131 is formed of latex rubber, or any similar plastic material having the requisite flexibility characteristics to permit bladder 131 of deformable housing 123 to function as hereinafter described. The plurality of beads 132 may be formed of styrofoam or any other plastic material. Bottom plate member 134, as well as all other components of head fixation device 120, including beads 132, are formed of any radiolucent material, whereby head fixation device 120 can be used with conventional x-ray or any other conventional types of imaging devices. The radiolucent material, such as any suitable plastic material should also have the requisite strength characteristics to permit the various components of head fixation device 120 to function as described herein, as well as be capable of being sterilized for use in an operating room.

Valve 133 is preferably threaded into an opening in bottom plate member 134 into fluid transmitting relationship with the interior 135 of bladder 131. Preferably, valve 133 is contained within a threaded tubular member 137, whereby valve 133, tubular member 137, bottom plate member 134 and bladder 131 may be adjusted as a unit by rotation of tubular member 137 within a mating threaded opening as will be hereinafter described in greater detail. A vacuum hose (not shown), which is commonly found in operating, treatment, and imaging rooms, may be attached to valve 133 to create a vacuum in bladder 131 and evacuate the air contained within bladder 131 through valve 133. Upon the air being evacuated from the interior 135 of bladder 131, the plurality of plastic beads 132 are frozen, or locked into, whatever spatial form, or shape, that has been imparted to the plurality of beads 132 and bladder 131 after bladder 131 of first deformable housing 123 has been deformed and conformed to the shape of the patient's nasion 125.

With reference to FIGS. 1-5, a means for adjustably positioning 140 the first deformable housing 123 with respect to frame 122 and the patient's nasion 125 is provided. The adjustable positioning means 140 preferably includes an elongate bar member 141 slidable within the frame 122 and includes means for securing 142 the bar member 141 with respect to the frame 122. Preferably, elongate bar member 141 has a dovetail cross-sectional configuration (FIG. 6) and the frame 122 has a mating slot 143, which also has a dovetail cross-sectional configuration, to slidingly receive elongate bar member 141. Securing means 142 may preferably comprise a locking thumb screw 144 received within frame member 122, and which may be threaded downwardly through frame 122 to abut against elongate bar member 141 and secure bar member 141 with respect to frame 122. Threaded tubular member 137 may be received within a threaded opening 138 formed in bar member 141, and by rotating tubular member 137, bladder 131 of first deformable housing 123 may be moved upwardly or downwardly with respect to bar member 141 to provide additional adjustments, if desired.

Figure 4:
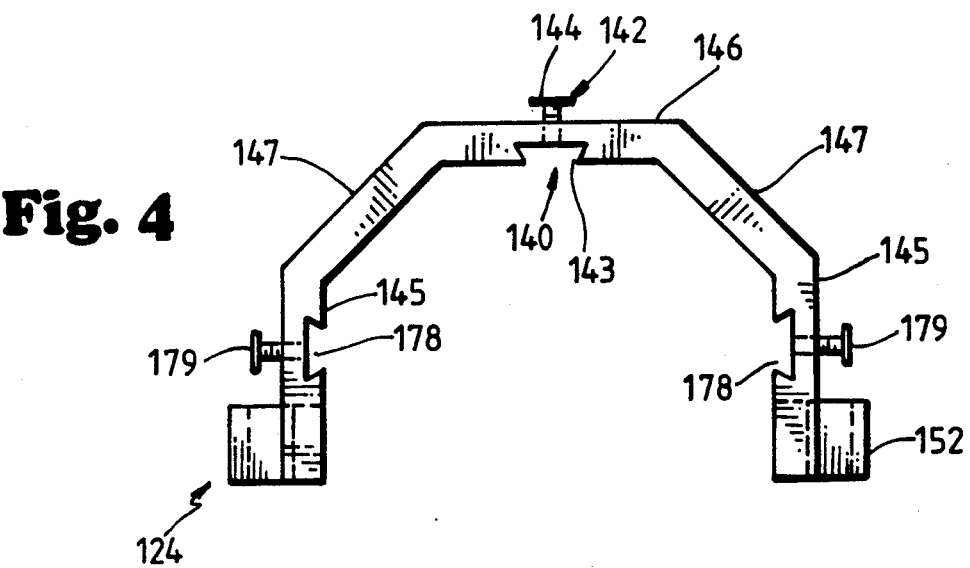
FIG. 4 is a front view of the frame of the noninvasive head fixation device of FIG. 1, in accordance with the present invention.

With reference to FIGS. 1-4, frame 122 is seen to preferably comprise two vertically disposed elongate members 145 and one horizontally disposed elongate cross-member 146, the first deformable housing 123 being mounted upon the horizontally disposed elongate cross-member 146. The two vertical members 145 are preferably connected to the horizontal cross-member 146 by angularly disposed connecting members 147, whereby frame 122 has a generally semi-hexagonal configuration as seen in FIGS. 1 and 4. The semi-hexagonal configuration readily permits first deformable housing 123 to be associated with frame 122 in an adjustable manner by the elongate bar member 141 of adjustable positioning means 142, and does not obstruct access to the patient's head 121 when performing the desired medical procedures, such as imaging or surgical procedures. Frame 122 may also include a planar base member 150 which may be provided with two upstanding posts 151 upon which are adjustably mounted the two vertical members 145 through the use of a vertical post guide block 152 attached to the lower end of each vertical member 145. Posts 151 may be frictionally received within vertical post guide blocks 152, or alternatively vertical post guide blocks 152 may be provided with conventional locking thumb screws 153 (FIG. 2) which can be tightened to fixedly secure vertical guide blocks 152 with respect to posts 151, whereby the height of first deformable housing 123 with respect to base member 150 can be adjusted. Base member 150 may be releasably secured to an operating or imaging table in any conventional manner, or alternatively an operating or imaging table could be provided with vertical posts 151 to accommodate the usage of head fixation device 120 with such tables.

Still with reference to FIGS. 1-4, the restraining means 124 associated with frame 122 for restraining rotational movement of the patient's head 121 may comprise at least one second deformable housing 160 associated with frame 122 and adapted to contact a portion of the patient's head 121. As seen in FIG. 2, the at least one second deformable housing 160 may include a flexible compressible bladder 161 which can conform to the shape of the portion of the patient's head 121 which contacts the second deformable housing 160. The at least one second deformable housing 160 may be mounted upon the base member 150 of frame 122 and be disposed in a diametrically opposed relationship from the first deformable housing 123, and is adapted to contact the underside 162 of the patient's head 121. The construction of flexible compressible bladder 161 of the at least one second deformable housing 160 is of identical construction to that of flexible bladder 131 as described in connection with FIG. 6A; however, its size may be larger, in that it is adapted to contact the underside 162 of the patient's head 121. A valve 163, similar in construction to that of valve 133, previously described, may be disposed upon the side of flexible bladder 162 in fluid communication with the interior flexible bladder 162, whereby a vacuum may be created in the bladder 162 to retain the shape imparted by the underside 162 of the patient's head 121 by prohibiting movement of the plurality of beads (not shown) contained within bladder 162.

Alternatively, as illustrated in FIGS. 1–3, the at least one second deformable housing 160 may include two compressible bladders 171 mounted upon frame 122, each of the two compressible bladders 171 being disposed in a plane 176 (FIG. 1) which is disposed substantially perpendicular to a plane 177 in which lies the first deformable housing 123, whereby the two compressible bladders 171 of the second deformable housing 160 will contact the sides of the patient's head 121, as will be hereinafter described in greater detail. Each of the compressible bladders 171 is of identical construction to flexible bladder 131 previously described in connection with FIG. 6A, and each flexible bladder 171 include a bottom plate member 174 valve member 173, with a plurality of small diameter beads (not shown) being contained in flexible bladders 171 as previously described. Each flexible bladder 171 of the second deformable housing 160 is adjustably positioned with respect to the frame 122 by an elongate member 175 having the same dovetail shaped cross-sectional configuration as elongate member 141 associated with first deformable housing 123. Each of the elongate members 173 is also slidably and adjustably received within frame 122, which include dovetail shaped openings 178 and locking screws 179. Compressible bladders 171 of the at least one second deformable housing 160 also each include a threaded member 172 in which is disposed valve 173 as previously described in connection with valve 133 and threaded member 137 of FIGS. 6 and 6A, whereby flexible bladder 171 may be moved inwardly and outwardly with respect to elongate member 175 as by rotation of threaded member 172, which is threadedly received within an opening formed in the end of elongate member 175.

Figure 9:
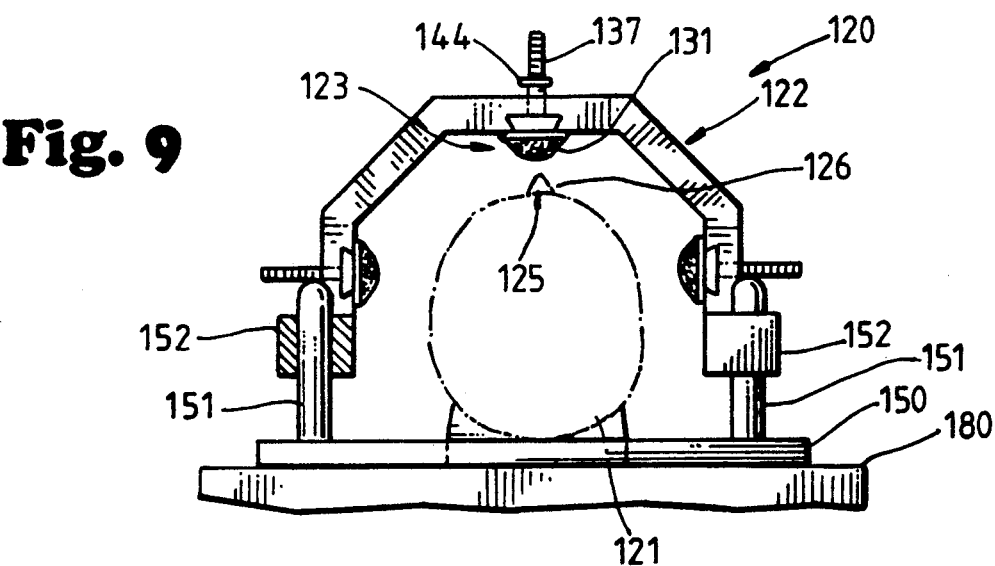
FIGS. 9-11 are front views of the device of FIG. 1 chronologically illustrating the noninvasive method of immobilizing a head in accordance with the present invention and utilizing the device illustrated in FIG. 1.
Figure 10:
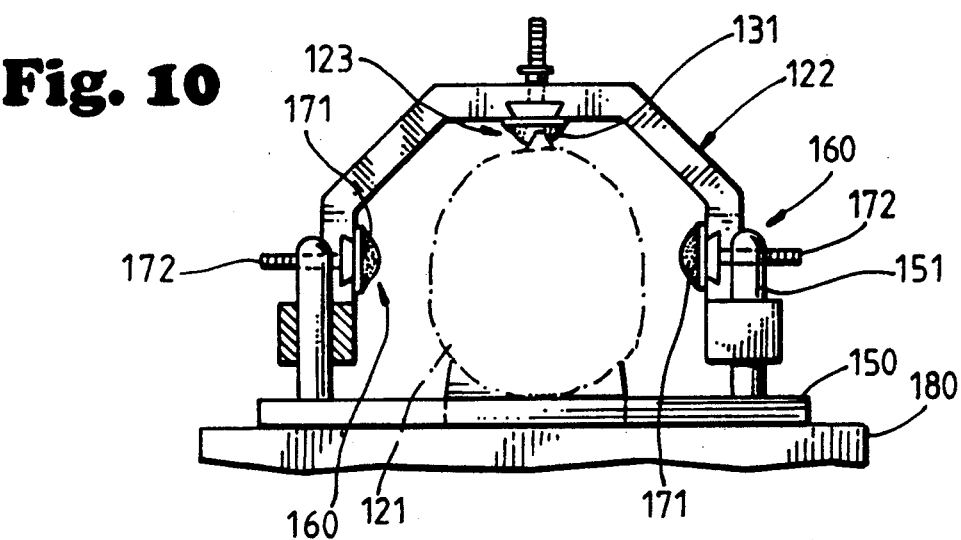
Figure 11:
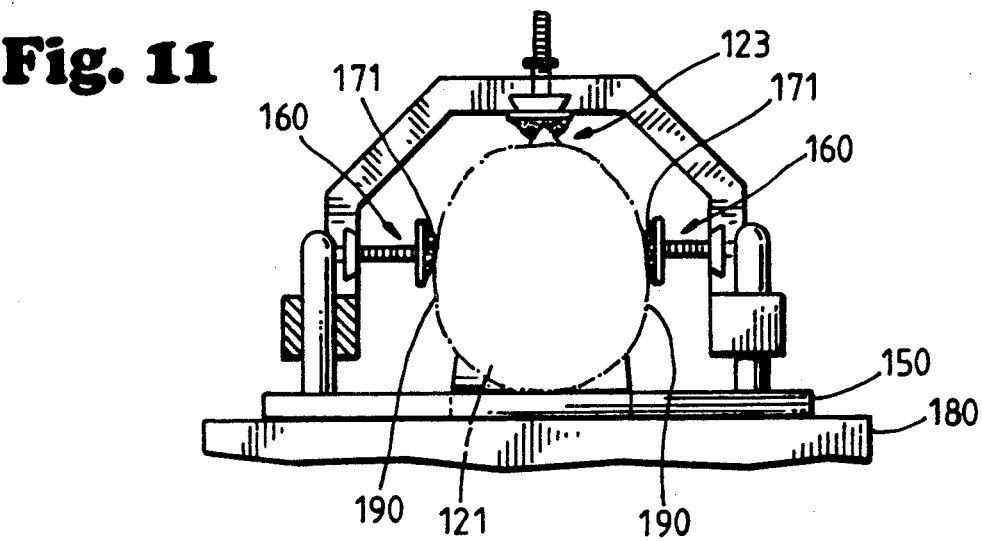

With reference now to FIGS. 9–11, the noninvasive method of immobilizing a patient's head 121 having a nasion 125, for use in medical procedures, will be described. The base plate 150 of frame 122 is secured to an operating or imaging table 180, or alternatively, table 180 is provided with two upstanding posts 151 as previously described. The patient then lays on table 180 with his or her head 121 laying upon base member 150. The semi-hexagonal frame 122 is then disposed upon posts 151 by use of vertical post guides 152, in order to dispose the first deformable housing adjacent the patient's head 121. As seen in FIGS. 2 and 9, first deformable housing 123 is disposed to overlie the patient's nasion 123 as by moving bar member 141 with respect to frame 122 until first deformable housing 123, or flexible, compressible bladder 131, is disposed above the patient's nasion 125. Frame 122 is then lowered downwardly along posts 151 until the first deformable housing 123 contacts the patient's nasion 125 and bladder 131 is deformed by nasion 125. Locking means, or thumb screws 153 (FIG. 2) on vertical post guide blocks 152 are engaged to fixedly secure the disposition of frame 122 with respect to the patient's head 121. The flexible, compressible bladder 131 of first deformable housing is then molded around the patient's nasion by a technician to deform the first deformable housing 123, or flexible and compressible bladder 131, to conform it to the shape of the patient's nasion 125. If necessary, additional adjustments may be made by rotating threaded member 137 to move flexible bladder 131 further downwardly, as seen in FIG. 10. The shape imparted to the first deformable housing 123 by the patient's nasion 125 is then retained by evacuating air from the interior of the flexible bladder 131 through valve 133 to create a vacuum in the bladder 131. The imparted shape is thus retained by prohibiting movement of the plurality of small diameter beads 135 contained within the bladder 131, at which time valve 133 is closed. The patient's head 121 is thus positioned in a reproducible location and orientation with respect to the frame 122 and operating or imaging table 180. As seen in FIG. 10, movement of the patient's head caused by the patient nodding his or her head 121 up and down is prohibiting by the engagement of nasion 125 with first deformable housing 123, but it is necessary to further restrain rotational movement of the patient's head 121, which could be caused by the patient moving his or her head back and forth from side to side.

Thus as seen in FIG. 11, rotational movement, or movement of the patient's head 121 from side to side, is thus restrained by utilizing at least one second deformable housing 160 to restrain such rotational movement. Flexible bladder 161 (FIG. 2) previously described could be used to contact the underside 162 of the patient's head 121, or alternatively the at least one second deformable housing 160 comprised of the two compressible bladders 171 previously described could be utilized. If flexible bladder 161 is utilized, it would also have air evacuated from the interior of bladder 161 in order to permit bladder 161 to conform to the shape of the underside 162 of the patient's head 121 in order to restrain the undesired rotational movement. If flexible bladders 171 are utilized, as illustrated in FIGS. 10 and 11, each flexible bladder 171 will be disposed adjacent the sides 190 of the patient's head 121 as by rotating threaded members 172 inwardly with respect to bar members 175, whereby flexible bladders 171 contact the sides 190 of the patient's head 121 and are deformed to conform to the shape of the sides 190 of the patient's head 121. Prior to moving flexible bladders 171 inwardly to contact the sides 190 of the patient's head 121, elongate bar members 175 are moved with respect to frame 122 to permit the flexible bladders 171 of the second deformable housing 160 to be disposed adjacent the desired side portion 190 of the patient's head 121, at which time securing means 179 or locking thumb screws 179 are engaged to secure bar members 175 with respect to frame member 122.

With the patient's head 121 thus fixated the imaging or surgical treatment procedure may be conducted. After the desired medical procedure has been completed, the flexible bladders 171 of the at least one second deformable housing 160, are moved outwardly from engagement with the patient's head 121, locking means 153 are disengaged to permit the lifting of frame 122 from the patient's head 121, and the patient may rise from table 180. Information about the positioning of the patient is preserved by the shape retained by the first deformable housing 123 which had been imparted to it by the patient's nasion 125. The first deformable housing 123 with the desired, retained shape, may be removed from frame 122 and stored for future use when it is necessary to reposition the patient's head 121 in the exact disposition and orientation with respect to table 180 that it had during the first medical procedure. By maintaining the vacuum within bladder 131 of first deformable housing 123, the desired shape may be retained. Alternatively, an impression of the first deformable housing 123 having retained the shape imparted to it by the patient's nasion 125 during a first medical procedure may be made in a conventional manner. The impression can be later used as a mold to permit another deformable housing, such as first deformable housing 123 to be formed, for use in a second medical procedure, in the shape of the patient's nasion 125 during the first medical procedure.

Figure 12:
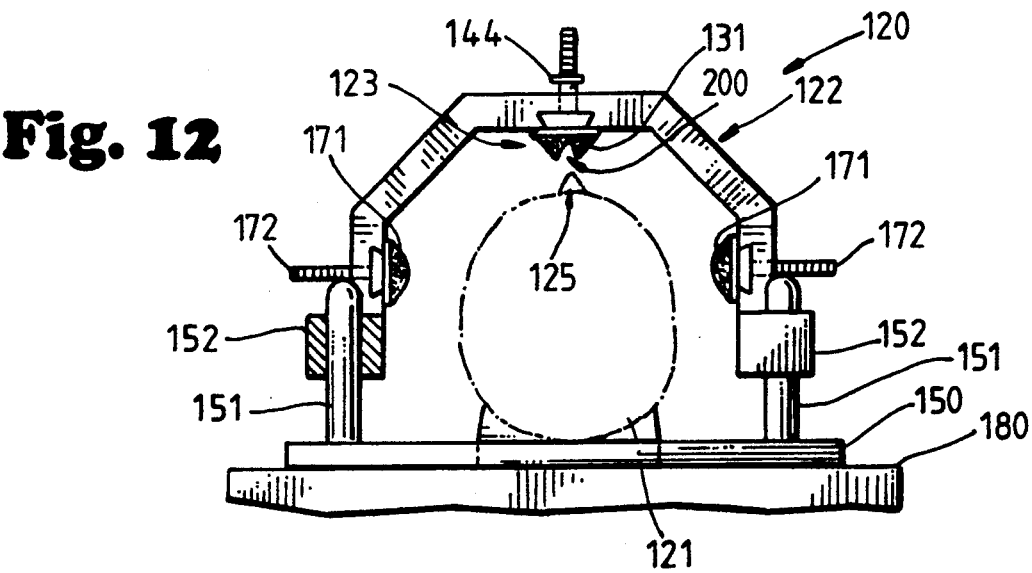
FIGS. 12-14 are front views of the device of FIG. 1, in accordance with the present invention, illustrating the device of FIG. 1 being utilized for a subsequent medical procedure.
Figure 13:
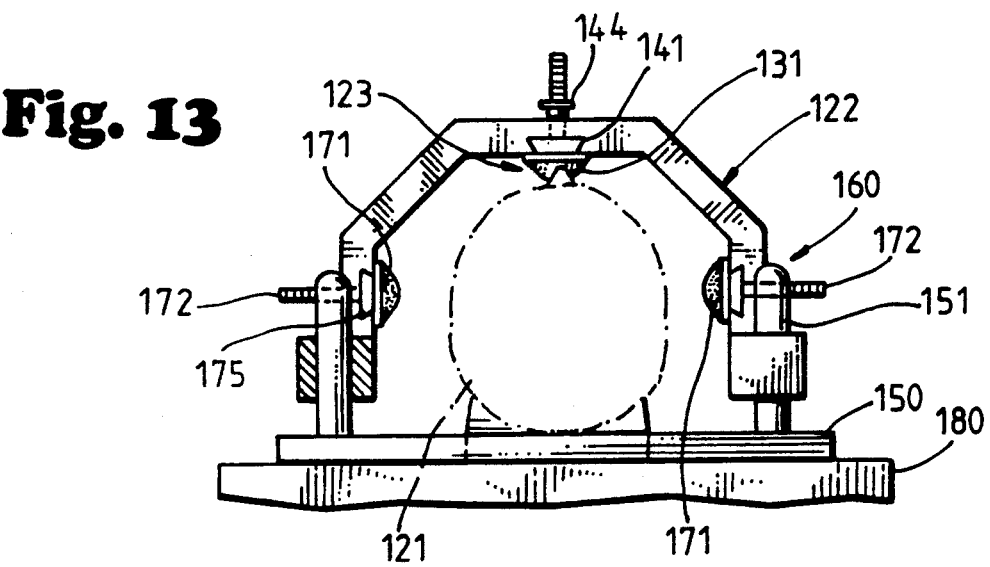
Figure 14:
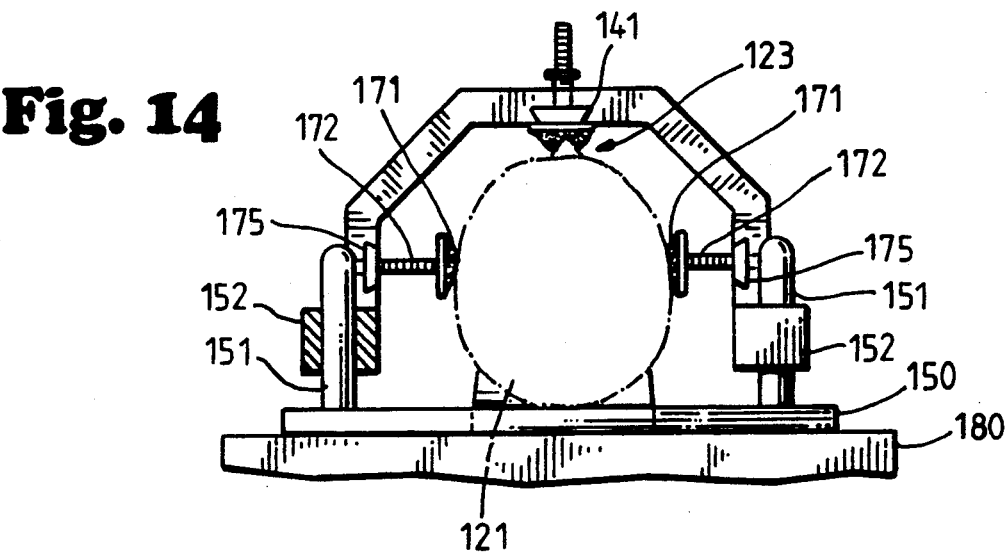

As illustrated in FIGS. 12-14, when it is desired to perform another medical procedure upon the patient's head 121, the patient's head is later disposed adjacent frame 122 for a second medical procedure in the same manner as previously described in connection with FIGS. 9-11. During the second or subsequent medical procedure, the first deformable housing 123 ,s nasion which is disposed to overlie and contact the patient 125, has the shape 200 previously imparted to it by the patient's nasion 125. When frame 122 is lowered, as previously described, to dispose the first deformable housing 123, having shape 200 formed therein, to contact the patient's nasion 125, the patient's head is moved by the technician until the patient's nasion precisely fits within first deformable housing 123. Rotational movement of the patient's head 121 is then restrained in the manner previously described, by contacting the patient's head with the at least second deformable housing 160. Thus, during the second, or subsequent medical procedure, the patient's head 121 has the precise orientation and disposition with respect to table 180 that head 121 had during the first, or any prior, medical procedure utilizing head fixation device 120. It should be noted that since there is no portion of head fixation device 120 associated with the mouth of the patient, intubation of the patient can be performed with the head fixation device 120 in place. If intubation is required, the patient may be first intubated, and then the head fixation device 120 be utilized in the manner previously described.

It is to be understood that the invention is not limited to the exact details of construction, operation, exact materials, or embodiment shown and described as obvious modifications and equivalents will be apparent to one skilled in the art; for example, the head fixation device of the present invention can also be converted for use with an invasive head fixation system, such as by using the head fixation device of the present invention to reposition the patient's head in the desired orientation, and then attaching a conventional fixation frame, at which time the head fixation device of the present invention may be removed. Accordingly, the invention is therefore to be limited only by the scope of the appended claims.

I claim:

1. A noninvasive head fixation device for use in medical procedures to immobilize a head of a patient having a nasion, comprising:

a frame, adapted to be disposed adjacent the patient's head;

a first deformable housing attached to the frame and means for positioning the first deformable housing to overlie and contact the patient's nasion, whereby its deformable housing may deform and conform to the shape of the patient's nasion, the first deformable housing including means for retaining the shape imparted to the first deformable housing by the patient's nasion; and means for restraining rotational movement of the patient's head, the restraining means being associated with the frame.

2. The noninvasive head fixation device of claim 1, wherein the first deformable housing includes a flexible and compressible bladder which can conform to the shape of the patient's nasion.

3. The noninvasive head fixation device of claim 2, wherein the bladder is fluid tight and contains a plurality of small diameter beads which are moveable within the bladder to permit the bladder to conform to the shape of the patient's nasion.

4. The noninvasive head fixation device of claim 3, wherein the shape retaining means includes a valve in fluid communication with the bladder, whereby a vacuum may be created in the bladder to retain the imparted shape by prohibiting movement of the plurality of beads contained within the bladder.

5. The noninvasive head fixation device of claim 2, further including means for adjustably positioning the first deformable housing with respect to the frame and the patient's nasion.

6. The noninvasive head fixation device of claim 5, wherein the adjustable positioning means includes an elongate, bar member slidable within the frame and, includes means for securing the bar member with respect to the frame.

7. The noninvasive head fixation device of claim 6, wherein the elongate bar member has a dovetail cross-sectional configuration and the frame has a mating slot having a dovetail cross-sectional configuration to slidingly receive the elongate bar member.

8. The noninvasive head fixation device of claim 1, where the frame includes two vertically disposed elongate members and one horizontally disposed elongate cross-member, the first deformable housing being mounted upon the horizontally disposed elongate cross-member.

9. The noninvasive head fixation device of claim 8, wherein the frame has a semi-hexagonal configuration wherein the two vertical members are each connected to the horizontal cross-member by an angularly disposed connecting member, one angularly disposed connecting member being disposed between each vertical member and the horizontal cross-member.

10. The noninvasive head fixation device of claim 9, wherein the vertical members are adjustably mounted upon a planar base member.

11. The noninvasive head fixation device of claim 1, wherein the restraining means comprises at least one second deformable housing associated with the frame and adapted to contact a portion of the patient's head, and includes a flexible compressible bladder which can conform to the shape of the portion of the patient's head which contacts the second deformable housing.

12. The noninvasive head fixation device of claim 11, wherein the at least one second deformable housing is a compressible bladder mounted upon the frame and is disposed in a diametrically disposed relationship from the first deformable housing and is adapted to contact the underside of the patient's head.

13. The noninvasive head fixation device of claim 12, wherein the bladder is fluid tight and contains a plurality of small-diameter beads which are moveable within the bladder to permit the underside of the bladder to conform to the shape of the patient's head.

14. The noninvasive head fixation device of claim 13, wherein the bladder includes a valve in fluid communication with the bladder, whereby a vacuum may be created in the bladder to retain the imparted shape by prohibiting movement of the plurality of beads contained within the bladder.

15. The noninvasive head fixation device of claim 11, wherein the at least one second deformable housing is two compressible bladders mounted upon the frame, each of the two compressible bladders being disposed in a plane which is disposed substantially perpendicular to a plane in which lies the first deformable housing, whereby the two compressible bladders of the second deformable housing contact are adapted to contact the sides of the patient's head.

16. A noninvasive method of immobilizing a head of a patient having a nasion, for use in medical procedures, comprising the steps of:
    disposing the patient's head adjacent a frame;
    disposing a first deformable housing associated with the frame to overlie and contact the patient's nasion;
    deforming the first deformable housing to conform to the patient's nasion;
    retaining the shape imparted to the first deformable housing by the patient's nasion; and
    restraining rotational movement of the patient's head.

17. The method of claim 16, including the step of utilizing a flexible and compressible bladder as the first deformable housing.

18. The method of claim 17, including the step of making the bladder fluid tight and filling the bladder with a plurality of small diameter beads which are moveable within the bladder.

19. The method of claim 18, including the steps of disposing a valve in fluid communication with the bladder; and creating a vacuum in the bladder to retain the imparted shape by prohibiting movement of the plurality of beads contained within the bladder.

20. The method of claim 17, including the step of adjustably positioning the first deformable housing with respect to the frame and the patient's nasion.

21. The method of claim 20, including the steps of adjustably positioning the first deformable housing by disposing it on an elongate bar member slidable within the frame; and securing the bar member with respect to the frame.

22. The method of claim 21, including the steps of providing the elongate bar member with a dovetail cross-sectional configuration; and providing the frame with a mating slot having a dovetail cross-sectional configuration to slidingly receive the elongate bar member.

23. The method of claim 16, including the steps of providing the frame with two vertically disposed elongate members and one horizontally disposed elongate cross-member; and mounting the first deformable housing upon the horizontally disposed elongate cross-member.

24. The method of claim 23, including the steps of forming the fame with a semi-hexagonal configuration; and connecting the each vertical member to the horizontal cross-member by an angularly disposed connecting member.

25. The method of claim 24, including the steps of adjustably mounting the vertical members upon a planar base member.

26. The method of claim 16, including the steps of utilizing at least one second deformable housing to restrain rotational movement of the patient'head and contacting a portion of the patient's head with the at least one second deformable housing which includes a flexible compressible bladder which can conform to the shape of the portion of the patient's head which contacts the second deformable housing.

27. The method of claim 26, including the steps of disposing the at least one second deformable housing in a diametrically disposed relationship from the first deformable housing; and contacting the underside of the patient's head with the at least one second deformable housing.

28. The method of claim 27, including the steps of making the bladder fluid tight and filling it with a plurality of small-diameter beads which are movable within the bladder to permit the bladder to conform to the shape of underside of the patient's head.

29. The method of claim 28, including the steps of providing the bladder with a valve in fluid communication with the bladder; and creating a vacuum in the bladder to retain the imparted shape by prohibiting movement of the plurality of beads contained within the bladder.

30. The method of claim 26, including the steps of utilizing as the at least one second deformable housing two compressible bladders mounted upon the frame; disposing each of the two compressible bladders in a plane which is disposed substantially perpendicular to a plane in which lies the first deformable housing; and contacting the sides of the patient's head with the two compressible bladders of the second deformable housing.

31. The method of claim 16, including the steps of:
    removing the patient's head from adjacent the frame, after completing the medical procedure;
    later disposing the patient's head adjacent the frame for a second medical procedure;
    disposing the first deformable housing associated with the frame to overlie and contact the patient's nasion, the first deformable housing having the shape previously imparted to it by the patient's nasion; and
    restraining rotational movement of the patient's head.

32. The method of claim 31, including the step of forming an impression of the first deformable housing having retained the shape imparted to it by the patient's nasion during a first medical procedure, whereby the impression can be later used as a mold to permit another deformable housing to be formed, for use in a second medical procedure, in the shape of the patient's nasion during the first medical procedure.

* * * * *